US00PP26989P3

(12) United States Plant Patent

Musacchi et al.

(10) Patent No.: US PP26,989 P3

(45) Date of Patent: Aug. 2, 2016

(54) PEAR TREE NAMED 'PE3UNIBO'

(50) Latin Name: ***Pyrus communis* L.**
Varietal Denomination: PE3UNIBO

(71) Applicant: Alma Mater Studiorum—Università di Bologna, Bolgona (IT)

(72) Inventors: Stefano Musacchi, Wenatchee, WA (US); Vincenzo Ancarani, Bologna (IT); Silviero Sansavini, Bologna (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 93 days.

(21) Appl. No.: 14/121,605

(22) Filed: Sep. 24, 2014

(65) Prior Publication Data

US 2015/0327415 P1 Nov. 12, 2015

(30) Foreign Application Priority Data

May 9, 2014 (QZ) ..... PBR 2014/0971

(51) Int. Cl.
*A01H 5/08* (2006.01)

(52) U.S. Cl.
USPC ..... Plt./176

(58) Field of Classification Search
USPC ..... Plt./176
See application file for complete search history.

(56) References Cited

PUBLICATIONS

PLUTO Plant Variety Database Feb. 19, 2016. p. 1.*

* cited by examiner

*Primary Examiner* — Annette Para
(74) *Attorney, Agent, or Firm* — Foley & Lardner LLP

(57) ABSTRACT

A new and distinct *Pyrus communis* L. pear tree variety named 'PE3UNIBO', is particularly characterized by the following features: medium vigorous and slightly compact trees with upright habitus; bearing habitus normally on spurs on 2-3 years old branches and sometimes on 1 year old shoot; good grafting compatibility with the main quince rootstocks; early medium ripening (about 1-2 days before 'Bartlett'); high and constant yield; early bearing; good size of fruit (about 200 g), ranging from pyriform to pyriform-elongated shape; green skin until the full ripening stage with a slight russet; tender and juicy white flesh at the full ripening stage with a very good flavor that is slightly sour; long storage capacity in cold room is, until 5 month.

5 Drawing Sheets

Latin name of the genus and species of the plant claimed: *Pyrus communis* L.

Variety denomination: 'PE3UNIBO'.

CROSS-REFERENCE TO RELATED APPLICATIONS

This application claims priority to European Community Plant Variety Office Plant Breeders' Rights Application No. 2014/0971 filed May 9, 2014.

BACKGROUND OF THE INVENTION

The present invention relates to a new and distinct variety of pear tree, botanically known as *Pyrus communis* L. of the Rosaceae family, and hereinafter referred to by the variety denomination 'PE3UNIBO'.

The new *Pyrus* variety is a product of a controlled breeding program conducted by the inventors, Stefano Musacchi, Silviero Sansavini and Vincenzo Ancarani, in Cadriano (Bologna), Italy. The variety is fully owned by Alma Mater Studiorum—Università di Bologna. The objective of the breeding program was to develop a new *Pyrus* variety with high yield, early-medium ripening, high fruit quality and long storability in cold room.

The new *Pyrus* variety originated from a cross made by the inventors in 1992 in Cadriano (Bologna), Italy. The female or seed parent is the *Pyrus communis* L. variety designated 'Abbé Fétel' (unpatented). The male or pollen parent is an unknown variety of *Pyrus communis* L. The new *Pyrus* variety was discovered and selected by the inventors within the progeny of the stated cross in a controlled environment in 2001 in Cadriano (Bologna), Italy.

Asexual reproduction of the new *Pyrus* variety by budding and grafting was first performed in August 2001 in Cadriano (Bologna), Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'PE3UNIBO' which in combination distinguish this pear tree as a new and distinct variety:

1. Trees with medium vigor;
2. Early-medium ripening;
3. Good graft compatibility with main quince rootstocks;
4. High and constant yield;
5. High quality fruit with good flavor;
6. Good fruit size;
7. Green skin; and
8. Long storage capacity In comparison to the parental variety 'Abbé Fétel', the claimed variety differs primarily in the traits listed in Table 1.

TABLE 1

| Trait | New Variety 'PE3UNIBO' | Female Parent 'Abbé Fétel' (unpatented) |
|---|---|---|
| Compatibility with main quince rootstock | Good | Partially |
| Fruit Shape | Pyriform - pyriform elongated; | Pyriform elongated |
| Fruit Size | Medium | Large |
| Skin color | Green | Yellow |
| Taste | Sweet and mildly sour | Sweet |
| Harvest time | Medium (1 days before 'Bartlett' pear) | Late (30 days after 'Bartlett' pear) |

Of the many commercial varieties known to the present inventors, the most similar in comparison to the new *Pyrus* variety 'PE3UNIBO' is the *Pyrus* variety 'Bartlett' (unpatented), in the following characteristics described in Table 2:

TABLE 2

| Characteristic | New Variety 'PE3UNIBO' | Comparison Variety 'BARTLETT' |
|---|---|---|
| Growth habit | Upright, slightly compact, fruit bearing on spur on 2-3 years old | Upright, fruit bearing on spur on 1 year old |
| Compatibility with main quince rootstock | Compatible | Incompatible |
| Skin color | Green | Green-yellow |
| Fruit Shape | Pyriform elongated | Pyriform with maximum diameter slightly toward calyx; irregular shape |
| Taste | Sweet and mildly sour | Sweet and sour |
| Size | Medium | Medium |
| Harvest time | Medium | Medium |

BRIEF DESCRIPTION OF THE DRAWINGS

The accompanying photographs illustrate the overall appearance of the new *Pyrus* variety 'PE3UNIBO' showing the colors as true as is reasonably possible with colored reproductions of this type. Colors in the photographs may differ slightly from the color values cited in the detailed botanical description, which accurately describe the color of 'PE3UNIBO'.

DETAILED BOTANICAL DESCRIPTION

Figure 1:
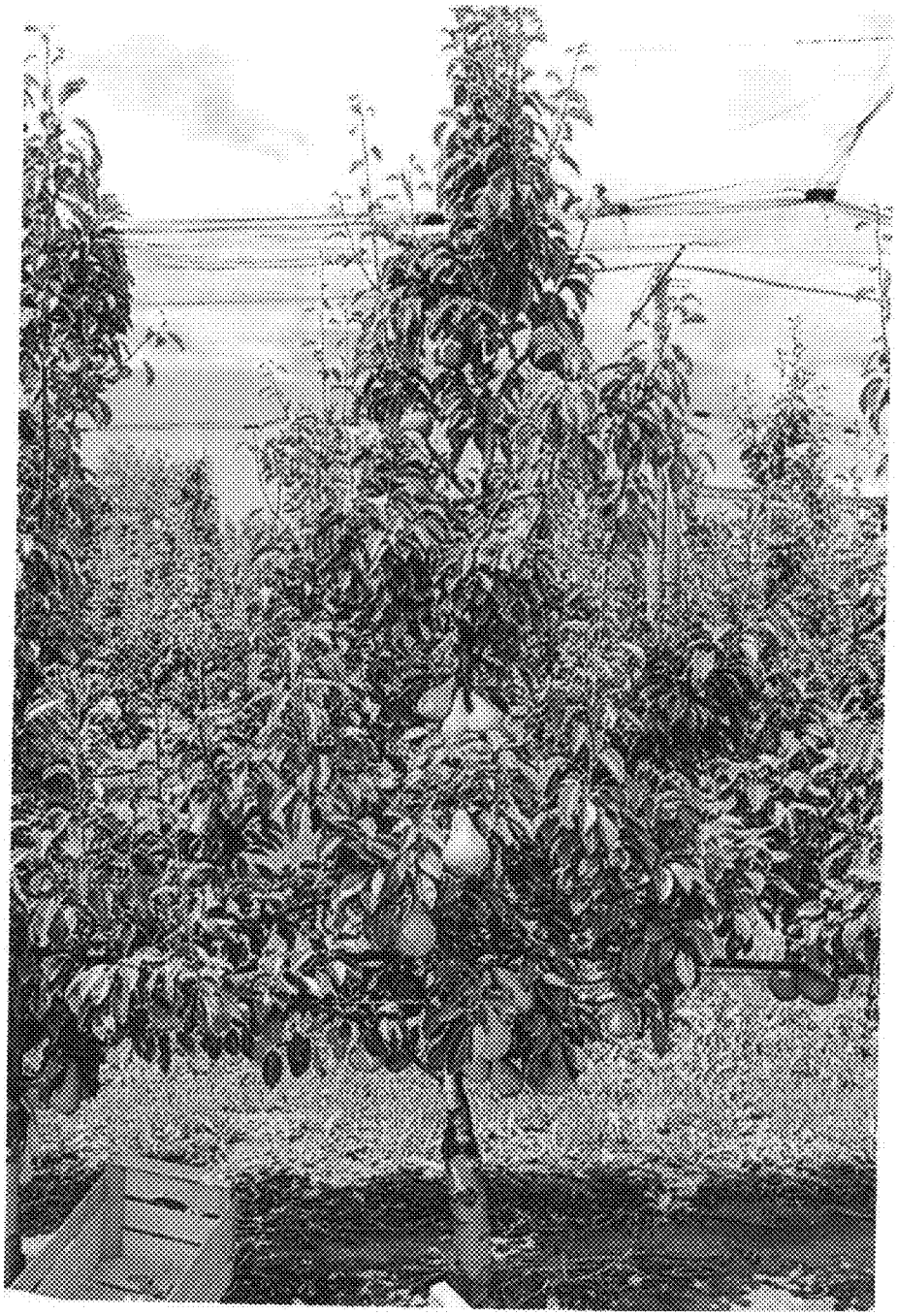
FIG. 1—shows a tree of 'PE3UNIBO', at six years old.
Figure 2:
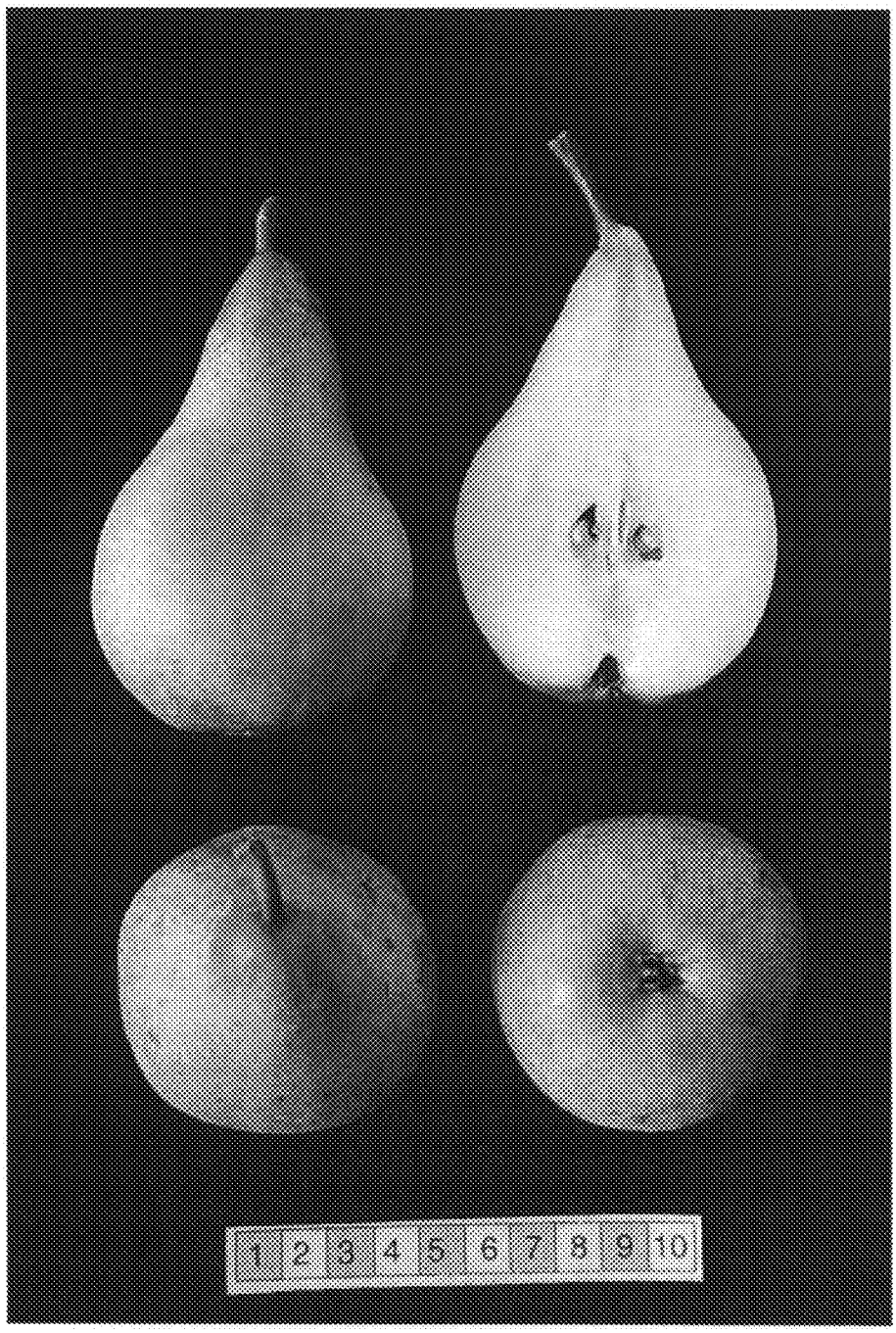
FIG. 2—shows typical fruits of 'PE3UNIBO'.
Figure 3:
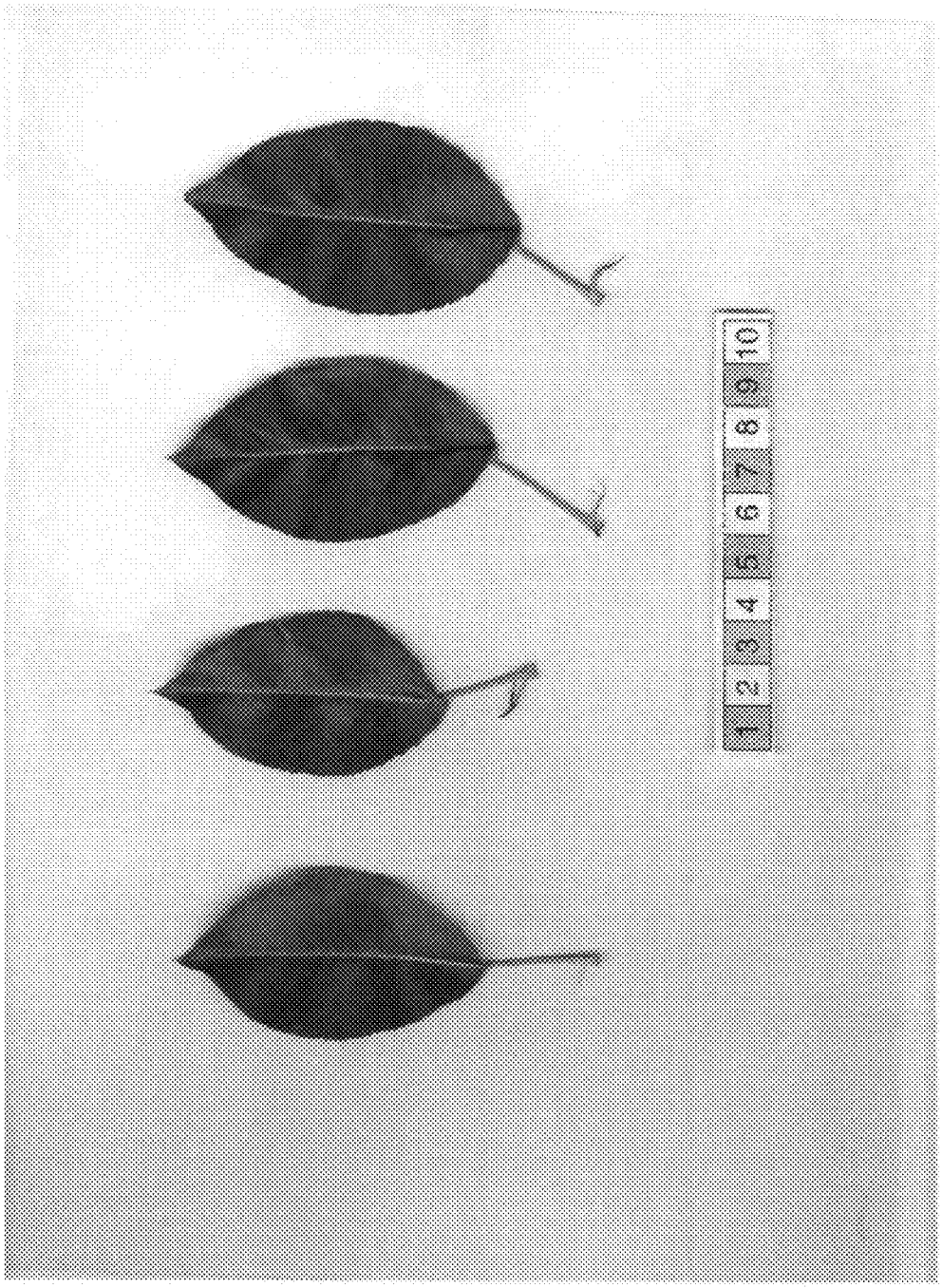
FIG. 3—shows the leaves of 'PE3UNIBO'.
Figure 4:
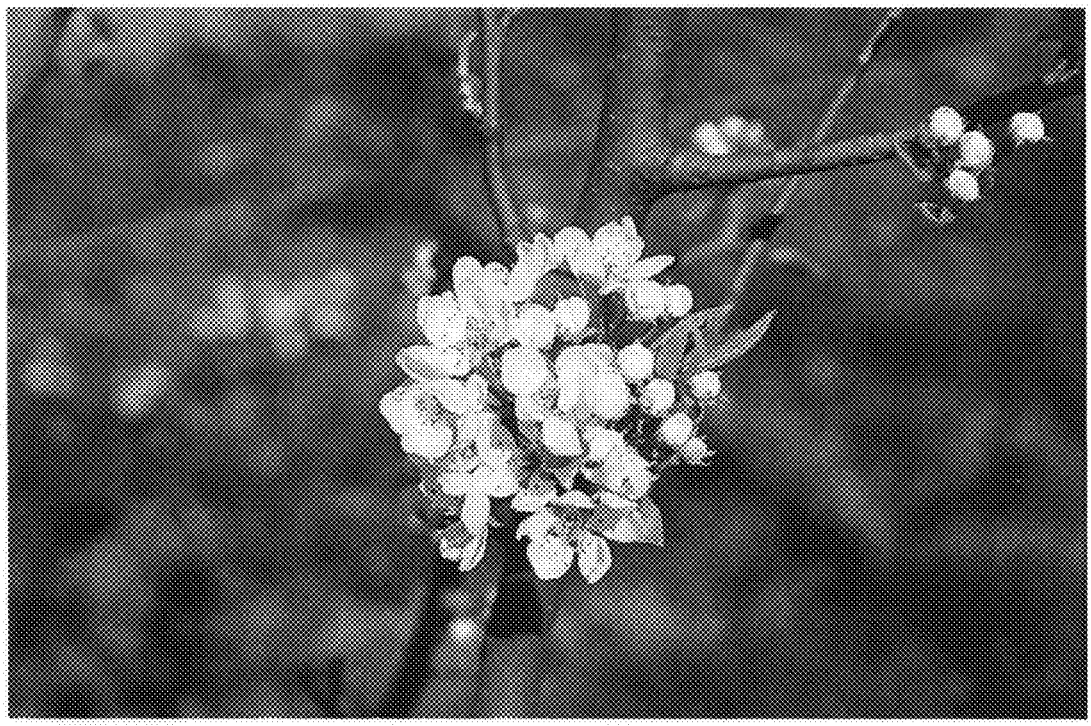
FIGS. 4 and 5—show different images of the flowers of 'PE3UNIBO', at full bloom.
Figure 5:
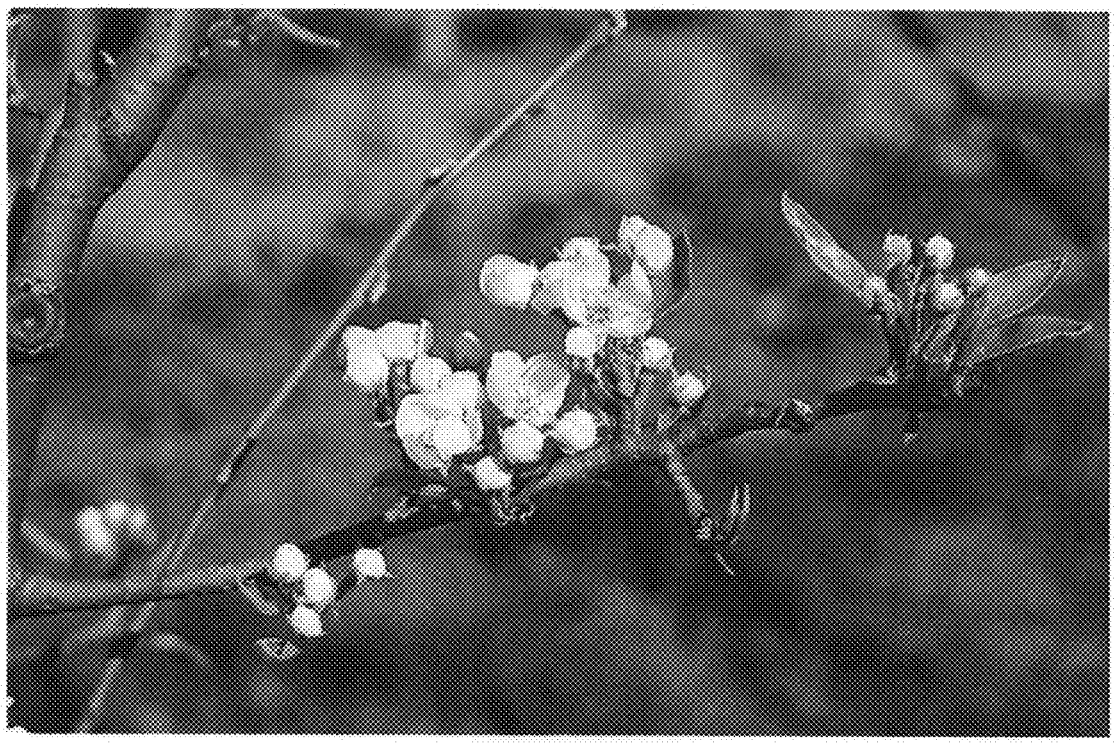

The new *Pyrus* variety 'PE3UNIBO' has not been observed under all possible environmental conditions. The phenotype of the new variety may vary with variations in environment such as temperature, light intensity, and day length without any change in the genotype of the pear tree.

The aforementioned photographs, together with the following observations, measurements and values describe trees of 'PE3UNIBO' as grown in the pear farm in Cadriano (Bologna), Italy, under conditions which closely approximate those generally used in commercial practice. The pear farm in which PE3UNIBO is growing has a clay soil; the climate is temperate continental with high summer temperatures and low winter temperatures; the orchard has a drip irrigation system used for fertigation.

Unless otherwise stated, the detailed botanical description includes observations, measurements and values based on 6 year old 'PE3UNIBO' trees grown in the pear farm in Cadriano (Bologna), Italy from 2009 to 2014. Quantified measurements are expressed as an average of measurements taken from a number of trees of 'PE3UNIBO'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately at 10:00 am in Cadriano (Bologna), Italy.

All of the trees of 'PE3UNIBO', insofar as they have been observed, have been identical in all the characteristics described below.

Classification:

*Botanical.*—*Pyrus communis* L.

*Commercial.*—*Pyrus* cv. PE3UNIBO.

Parentage:

*Female or seed parent.*—*Pyrus communis* L. variety designated 'Abbé Fétel' (unpatented).

*Male or pollen parent.*—Unknown variety of *Pyrus communis* L.

Propagation: Budding and grafting.

Growing conditions:

*Light intensities.*—Full sunlight.

*Temperature* (*in the vegetative season, from March to September, year* 2013).—Minimum: 0.1° C. in March. Maximum: 38.9 ° C. in August. Medium: 8° C. (March) to 26.3° C. (July).

*Fertilization.*—A balanced fertilizer with level of N 80 kg/ha; $P_2O_5$ 50 kg/ha; $K_2O$ 120 kg/ha.

*Growth regulators.*—Not used.

*Pruning or trimming requirements.*—Winter pruning.

Tree:

*Age.*—Observed trees were six years old and grafted on quince Rootstock BA29.

*Vigor.*—Medium vigor and slightly compact; early bearing; quite late and abundant flowering; high and constant productivity; no biennial bearing. The variety is compatible with the main quince and pear rootstocks.

*Type of bearing.*—Typically on spurs on 2-3 years old branches and sometimes on 1 year old shoot.

*Form.*—Upright and conical: branches inserted with a narrow crotch angle. Form also depends on the training system used.

*Habit.*—A medium sized tree with one trunk and one leader; main branches spreading laterally upward but the new growth is fastigiate; symmetrical crown and rounded shape. Predominantly the new shoots are medium-short (these ones have short internode length), nevertheless some long shoots can grow.

*Branching habit.*—Main branches angle is 15° to 65° with respect to trunk if allowed to grow naturally. The crotch angle changes along the trunk: the basal branches have a more right crotch angle whereas the upper and apical branches have a more narrow crotch angle.

*Density.*—High density of the canopy.

*Size at maturity.*—Height: About 3.04 m. Spread: About 1.25 m.

*Trunk.*—Height (up to leaders): About 2.64 m. Diameter: About 44.8 mm. Texture: At first, it is smooth with numerous and irregular lenticels (from rounded to elongated) also arranged vertically to form a vertical lines of pustules; then the surface appearance shows some grooves. Bark color: Primarily RHS 197D, with RHS 172B, underbark. Trunk Lenticels: Length: About 2.97 mm (from 0.95 to 6.03 mm). Width: About 1.74 mm (from 1.11 to 2.66 mm). Color: RHS 197A. Density: 2.48 n°/cm$^2$.

*Branches* (*on trees in the* 6$^{th}$ *year*).—Number per tree: About 15 (from 11 to 17). Length: Varies due to pyramidal shape of tree; maximum of 86 cm to 110 cm; minimum of 10 cm to 65 cm. Diameter: About 10.7 mm to 29.7 mm. Surface texture: vary from smooth with numerous lenticel to rough. Pubescence: Absent. Color: Mature (after about 3 years old): Primarily RHS 197B, with RHS 199A underbark. New Growth: RHS 199A. Internode length (in the middle of branches): Long shoot: About 3.5 cm to 5.5 cm. Short shoot: About 1.5 cm to 3.5 cm. Internode diameter (in the middle of branches): Long shoot: About 5.13 mm to 6.43 mm. Short shoot: About 4.72 mm to 5.68 mm. Branch lenticels (rounded shape): Length: About 1.68 mm. Width: About 2.30 mm. Color: RHS 165B. Density: 3.42 n°/cm$^2$. One Year old Shoot lenticels (small and elongated): Length: About 1.2 mm to 1.3 mm. Width: About 0.84 mm to 1.01 mm. Color: RHS 199C. Density: 71 n°/cm$^2$.

*Spur.*—Present: Yes. Distance between each spur: On the 3 years old branches, the distance is about 2 mm to 5.5 mm. Diameter of each spur: About 4.37 mm. Number of fruit per spur: About 2 to 4.

*Leaves.*—Arrangement: Alternate, simple, petiolated and arranged outwards in relation to shoot.

*Lamina.*—Size: Length: About 6.1 mm (from 4 to 8.6 mm fully expanded leaf). Width: About 3.7 mm (from 2.5 to 5.6 mm fully expanded leaf). Length/width ratio: 1.6. Overall Shape: the shape of leaf blade is "oval" with a medium-short pointed tip; the leaf area is medium: 20 cm$^2$; the longitudinal axis is slightly curved. Base shape: slightly obtuse. Apex shape: right-angled. Margin: bluntly serrate. Texture: Upper surface: glabrous. Under surface: glabrous. Pubescence: Upper surface: absent. Under surface: absent. Color (mature leaves): Upper surface: RHS 147A. Under surface: RHS 147C. Color (immature leaves): Upper surface: RHS 144A. Under surface: RHS 166D.

*Venation.*—Type: pinnate venation from central vein to the leaf edge. Color: RHS 151A.

*Petiole.*—Length: About 2.9 mm . Diameter: About 0.9 mm. Color: RHS 151A.

*Stipule.*—Arrangement: present; the distance from basal attachment of petiole is on average. Length (distance of stipules from basal attachment of petiole): About 10 mm to 15 mm. Width: About 10.2 mm.

Inflorescence:

*Blooming time.*—Full bloom on about April 3$^{rd}$ (late and fast flowering).

*Blooming period.*—About 7 to 10 days.

*Fragrance.*—Not detected.

*Type.*—Corymb.

*Number of flowers per inflorescence.*—About 4 to 6.

*Inflorescence size.*—Diameter: About 5 cm. Depth: About 4 cm.

*Buds* (*vegetative bud on* 1 *year old shoot*).—Terminal Buds: Number per spur: About 1 to 2. Shape: medium-large and pointed. Length: About 8.1 mm. Width: About 4.3 mm. Color: Apex, RHS 200D, and base, RHS 200B. Texture: quite swollen bud support. Pubescence: slight pubescence was observed. Lateral Buds: Number per spur: About 1. Shape: long with acute apex; the position of vegetative bud in relation to shoot is held out; the bud support is medium-large sized. Length: About 6.33 mm. Width: About 3.27 mm. Color: Apex, RHS 200D and base, RHS 200B. Texture: smooth. Pubescence: not observed. Flower Buds (on 2-3 years old branches): Number per spur: 1. Shape: large and pointed. Length: About 8.23 mm. Width: About 3.36 mm. Color: Apex, RHS 200D, and base, RHS 200D. Texture: smooth. Pubescence: Absent.

*Petals.*—Number per flower: Five. Size: medium. Overall shape: the margins of petals touch each other. Apex shape: rounded. Base shape: rounded. Texture (upper surface): smooth. Texture (lower surface): smooth. Margin: entire. Color (upper surface): White at full bloom. Color (lower surface): White at full bloom.

*Sepals.*—Number per flower: Five.

*Pollination requirements.*—Can be pollinated by several varieties of pear trees.

Fruit:

*Keeping quality.*—The fruit keeps well on the tree; The fruit can be stored in cold temperature conditions for up to 5 months without loss of firmness and juiciness. The shelf life ranges from one week to ten days without having a loss of firmness and juiciness.

*Maturity when described.*—Ripe for eating.

*Maturity period after full bloom.*—About 129 days after full bloom, on August 9$^{th}$.

*Type.*—Pome.

*General shape.*—Slightly irregular from pyriform to pyriform elongated, with the maximum diameter clearly towards calyx; the fruit profile is concave. The stem is from medium to medium-large, sometime without the stalk cavity.

*Average weight.*—About 223 g.

*Fruit size.*—Average height: About 105.6 mm. Average diameter (at widest point): About 70.9 mm. Height/thickness ratio: 1.5.

*Stem.*—Length: About 19.0 mm. Diameter: About 4.6 mm. Color: RHS 199A.

*Basin.*—Depth: About 2.17 mm. Width: About 8.5 mm.

*Calyx.*—Depth: About 6.45 mm. Width: About 7.69 mm. Crowning at calyx end: weak to medium. Calyx tube: Closed (it does not communicate with locules). At harvest the sepal are converging.

*Skin.*—Thickness: medium thin. Texture: Smooth with numerous little lenticels, with 15-20% of fine russet; predominantly localized at the top of the fruit and around the calyx. Color: RHS 144C (at picking time);

RHS151B (full ripe). Lenticels: very small and round, point shape; not measured. Color: RHS 199B. Density: 36.4 n°/cm$^2$.

*Flesh.*—Firmness (at picking time): 5.5 to 6.0 kg (measured with an 8 mm tip). Color: RHS 155A. Texture: fine, tender and juicy; some veining in the flesh. Aroma: quite aromatic, good flavor and sour taste. Sugar content (at picking time): 13.1 to 14.4° Brix. Acidity/Starch (at picking time) 4.98 to 5.30 g/lt malic acid. Core: Symmetry of core: slightly asymmetric. Distinctness of core lines: medium. Locules: Number (per fruit): 5. Length: About 13 mm. Width: About 8 mm. Form: the seed fills almost the locule cavity.

Seeds:

*Number per fruit.*—About 1 to 10.

*Number per locule.*—About 2.

*Shape.*—Elliptic.

*Length.*—About 8 mm.

*Width.*—About 4 mm.

*Texture.*—Smooth.

*Color.*—RHS 200B.

Use: Fresh market.

Disease/pest resistance: Unknown; test for tolerance to Fire Blight (*Erwinia amylovora*) in progress.

Disease/pest susceptibility: None observed.

Winter hardiness: No winter cold damage to wood and buds of dormant pear trees have been observed in during the years of evaluation; but open flowers and young fruitlets are killed by exposure to −1.5 to −3° C., depending on the length of exposure.

Drought/heat tolerance: Tolerant to temperatures up to 38° C., growth is limited by drought periods without irrigation.

What is claimed is:

1. A new and distinct variety of *Pyrus communis* L. pear tree named 'PE3UNIBO', as illustrated and described herein.

* * * * *